United States Patent
Clayton et al.

(10) Patent No.: US 8,162,999 B2
(45) Date of Patent: *Apr. 24, 2012

(54) ECTOPARASITE ERADICATION METHOD AND DEVICE

(75) Inventors: Dale H. Clayton, Salt Lake City, UT (US); Joseph S. Atkin, Salt Lake City, UT (US); Kevin G. Wilding, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/875,911

(22) Filed: Sep. 3, 2010

(65) Prior Publication Data

US 2010/0331931 A1    Dec. 30, 2010

Related U.S. Application Data

(63) Continuation of application No. 11/286,155, filed on Nov. 23, 2005, now Pat. No. 7,789,902, which is a continuation-in-part of application No. 11/133,067, filed on May 18, 2005, now abandoned.

(60) Provisional application No. 60/572,842, filed on May 19, 2004.

(51) Int. Cl.
*A61F 7/00* (2006.01)
*A61M 1/20* (2006.01)
*A45D 20/50* (2006.01)

(52) U.S. Cl. ...................... 607/104; 43/132.1
(58) Field of Classification Search .................. 607/104; 43/132.1
See application file for complete search history.

(56) References Cited

U.S. PATENT DOCUMENTS

| | | | |
|---|---|---|---|
| 3,721,250 A | 3/1973 | Walter et al. |
| 4,794,225 A | 12/1988 | Maese |
| 4,961,283 A | 10/1990 | Forbes |
| 5,261,427 A | 11/1993 | Dolev |
| 5,279,256 A | 1/1994 | Brite |
| 5,343,881 A | 9/1994 | Golan et al. |
| 5,526,578 A | 6/1996 | Iyer |
| 5,628,332 A | 5/1997 | Debourg et al. |
| 5,918,607 A | 7/1999 | Zucker |

(Continued)

FOREIGN PATENT DOCUMENTS

DE    2508951    2/1975

(Continued)

OTHER PUBLICATIONS

Hiraoka, Tauyoshi et al., "Thermotolerance of human body louse, *Pediculus humanus corporis*, 1: Treatment of adults and eggs by hot water", Jpn. J. Sanit. Zool., 1995 pp. 77-79-vol. 46, No. 1.

(Continued)

*Primary Examiner* — Roy Gibson
*Assistant Examiner* — Kaitlyn Smith
(74) *Attorney, Agent, or Firm* — Phillips Ryther & Winchester; Matthew D. Thayne

(57) ABSTRACT

A method of eliminating an ectoparasite infestation is disclosed that may include steps of defining a target area on an animal having an ectoparasite infestation, heating a volume of air to a temperature to form heated air, applying the heated air to the target area with an airflow such that the heated air impinges directly on substantially all ectoparasites located within the target area, and maintaining the heated air at the target area for a period of time sufficient to affect an ectoparasite mortality rate of at least 50%.

20 Claims, 3 Drawing Sheets

U.S. PATENT DOCUMENTS

| | | | |
|---|---|---|---|
| 6,006,758 | A | 12/1999 | Thorne |
| 6,053,180 | A | 4/2000 | Kwan |
| 6,141,901 | A | 11/2000 | Johnson et al. |
| 6,265,384 | B1 | 7/2001 | Pearlman |
| 6,425,403 | B1 | 7/2002 | Lin Lu et al. |
| 6,678,994 | B2 | 1/2004 | Topp |
| 6,685,969 | B2 | 2/2004 | Van Scoik et al. |
| 2002/0194773 | A1 | 12/2002 | Topp |
| 2005/0013727 | A1 | 1/2005 | Hedman |
| 2008/0212312 | A1 | 9/2008 | Kaufmann et al. |
| 2010/0049286 | A1 | 2/2010 | Thorsen |
| 2010/0071713 | A1 | 3/2010 | Simon et al. |
| 2010/0086577 | A1 | 4/2010 | Munoz et al. |
| 2010/0145417 | A1 | 6/2010 | Kaufmann et al. |

FOREIGN PATENT DOCUMENTS

| | | |
|---|---|---|
| EP | 1 036 522 A2 | 9/2000 |
| WO | WO99/52410 | 10/1999 |
| WO | WO 01/52689 A1 | 7/2001 |

OTHER PUBLICATIONS

Kobayashi, Mutsuo et al., "Thermotolerance of human body louse, *Pediculus humanus corporis*, 2: Preliminary evaluation of hot air for killing adults and eggs", Jpn. J. Sanit Zool., 1995 pp. 83-86, vol. 46, No. 1.

Pearlman, Dale Lawrence, MD, A Simple Treatment for Head Lice: Dry on, Suffocation-Based Pediculicide, Pediatrics, Sep. 3, 2004, vol. 114, No. 3.

Clayton Lab Projects—CASPeR (Center for Alternate Strategies of Parasite Removal), "The Little Lousebuster That Could", Dec. 2009.

Goates, Brad M. et al., "An Effective Nonchemical Treatment for Head Lice: A Lot of Hot Air", *Pediatrics—Official Journal of the American Academy of Pediatrics*, Nov. 3, 2006.

International Preliminary Report on Patentability mailed Nov. 29, 2007 in PCT Application No. PCT/US06/19466.

International Preliminary Report on Patentability mailed Nov. 30, 2006 in PCT Application No. PCT/US05/17969.

International Search Report and Written Opinion mailed Mar. 30, 2006 in PCT Application No. PCT/US05/17969, filed May 19, 2005.

International Search Report and Written Opinion mailed Jul. 20, 2007 in PCT Application No. PCT/US06/19466, filed May 18, 2006.

Office Action mailed Nov. 24, 2008 in U.S. Appl. No. 11/286,155, filed Nov. 23, 2005.

Office Action mailed Jul. 17, 2009 in U.S. Appl. No. 11/286,155, filed Nov. 23, 2005.

Office Action mailed Jun. 1, 2007 in U.S. Appl. No. 11/133,067, filed May 18, 2005.

Office Action mailed Nov. 23, 2007 in U.S. Appl. No. 11/133,067, filed May 18, 2005.

Office Action mailed Feb. 26, 2009 in U.S. Appl. No. 11/133,067, filed May 18, 2005.

Notice of Allowance mailed May 7, 2010 in U.S. Appl. No. 11/286,155, filed Nov. 23, 2005.

Supplementary European Search Report dated Mar. 29, 2010 in European Application No. 06770668.9.

Office Action mailed Aug. 6, 2010 in U.S. Appl. No. 12/548,264, filed Aug. 26, 2009.

Office Action mailed Nov. 24, 2008 in U.S. Appl. No. 12/548,264, filed Aug. 26, 2009.

Office Action dated Feb. 15, 2011 in European Application No. 06770668.9.

ECTOPARASITE ERADICATION METHOD AND DEVICE

RELATED APPLICATIONS

This application is a continuation of U.S. patent application Ser. No. 11/286,155, filed on Nov. 23, 2005 now U.S. Pat. No. 7,789,902, which is a continuation-in-part of U.S. patent application Ser. No. 11/133,067, filed on May 18, 2005 now abandoned, which claims priority from U.S. Provisional Patent Application No. 60/572,842 filed May 19, 2004, each of which are hereby incorporated by reference.

FIELD OF THE INVENTION

The present invention relates generally to the elimination of ectoparasites. More particularly, the present invention relates to utilizing heated forced air to eliminate ectoparasites.

BACKGROUND OF THE INVENTION

Over the past decade, cases of head lice have been increasing rapidly throughout the world, with an estimated ten million cases per year in the U.S. alone. Head lice, *Pediculus capitis*, are a major irritant to children and their parents. *P. capitis* have three life stages, including an egg stage, three juvenile instars, and an adult stage. Head lice infestations cause children to miss an estimated 12-24 million days of school per year. Ridding a person of head lice is an extremely difficult and frustrating task. Indeed, some families, particularly in developing countries, have chronic infestations that are never eradicated. Head lice and body lice, *P. humanus*, are extremely similar genetically, and recent research suggests that they may be members of the same species. The similarity of head lice to body lice is cause for concern because body lice vector several human diseases, including epidemic typhus and relapsing fever, diseases that killed many millions of people during the $20^{th}$ century.

Several methods of treatment for head lice infestations are currently available, including pesticidal shampoos, specialized louse combs and home remedies. Many of these treatments may be inefficient in eliminating head lice infestations. For example, specialized shampoos have never been shown to effectively kill eggs, and hatched lice have begun to evolve resistance to most of them. The use of a louse comb to comb the hatched lice and eggs out of an individuals hair can be effective, but is very time intensive and tedious to use. Most parents do not have the patience to eliminate the infestation in this manner. Additionally, hot air treatments have been suggested as a possible treatment for lice. However, though hot air has been shown to kill lice and their eggs in vitro, such treatments are generally ineffective in vivo.

A method of eradicating head lice infestations is needed that effectively kills both hatched lice and their eggs, but is safe, reliable, and easy to use. Additionally, it would be desirable that such a method utilize non-chemical means to prevent the lice from developing resistances to the treatment and avoid any undesirable side effects to the patient.

SUMMARY OF THE INVENTION

It has been recognized that it would be advantageous to develop a reliable, non-chemical treatment for eradicating head lice and other ectoparasites. A method of eliminating an ectoparasite infestation is disclosed that may include steps of defining a target area on an animal having an ectoparasite infestation, heating a volume of air to a temperature to form heated air, applying the heated air to the target area with an airflow such that the heated air impinges directly on substantially all ectoparasites located within the target area, and maintaining the heated air at the target area for a period of time sufficient to affect an ectoparasite mortality rate of at least 50%.

In another embodiment of the present invention, an institutional method for eliminating an ectoparasite infestation is disclosed. The method may include steps of defining a target area on a human having an ectoparasite infestation, heating a volume of air to a temperature of from about 50° C. to about 100° C. to form heated air, applying the heated air to the target area with an airflow of from about 45 ft$^3$/min to about 365 ft$^3$/min, such that the heated air impinges directly on substantially all ectoparasites located within the target area, and maintaining the heated air at the target area for from about 5 seconds to about 1 hour.

The present invention may include methods to increase the impingement of the heated air on the ectoparasites located within the target area. In one aspect, a method may include steps of determining that the human having an ectoparasite infestation has a hair length suitable for sectioning, dividing the hair into a number of discrete sections to expose a plurality of scalp areas, and sequentially applying the heated air to each discrete section of hair associated with each of the plurality of scalp areas. In another aspect, a method may include a step of systematically applying heated air to the target area utilizing a comb device to separate and lift hair within the target area.

In yet another embodiment of the present invention, a handheld method for eliminating an ectoparasite infestation is disclosed. The method may include steps of defining a target area on a human having an ectoparasite infestation, heating a volume of air to a temperature of from about 50° C. to about 100° C. to form heated air, applying the heated air to the target area with an airflow of from about 20 ft$^3$/min to about 220 ft$^3$/min such that the heated air impinges directly on substantially all ectoparasites located within the target area, and maintaining the heated air at the target area for a period of time sufficient to affect an ectoparasite mortality rate of at least 50%.

Additional features and advantages of the invention will be apparent from the detailed description which follows, taken in conjunction with the accompanying drawings, which together illustrate, by way of example, features of the invention.

DETAILED DESCRIPTION

Figure 1:
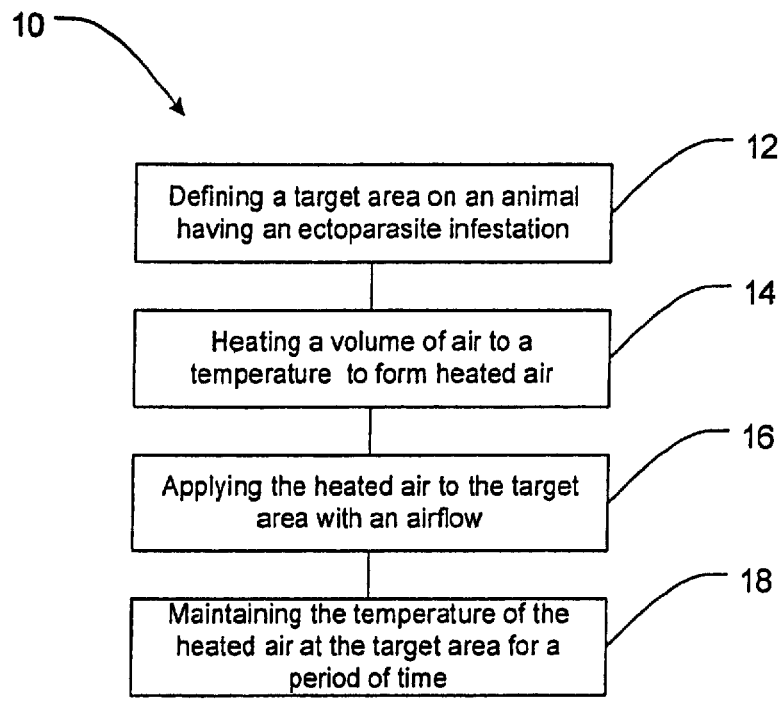
FIG. 1 is a flow chart of a method of eliminating head lice in accordance with an embodiment of the present invention.

In the previously filed U.S. patent application Ser. No. 11/133,067, airflow ranges were presented that were obtained using a pitot tube anemometer, as is common in the art. Further testing has indicated, however, that such measurements may be in error, and are thus inaccurate. Interestingly, reported measurements for airflow from various manufacturers of blow dryers vary widely, as is discussed in the examples below. These reported measurements appear to be mere marketing tools for blow dryer manufactures. As such, this continuation-in-part has been filed to correct the inaccurate airflow range values reported in the above referenced parent application. The following airflow ranges are intended to be volumetric measurements, examples of which are described in the Examples section below. The high and the low endpoints to the airflow ranges have been shifted downward to accommodate the newly measured airflow values, but the size of each range has been maintained for consistency. It should be noted that the previously reported inaccurate airflow range values were merely innocent errors based on what was believed to be standard measurement practices in the art. Reliance on these flawed standard measurement practices resulted in the inaccurate airflow range values. As such, the airflow ranges have been modified but the novel aspects of the present invention are unchanged.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Though the following discussion is focused primarily on head lice, it should be noted that numerous species of ectoparasites can be killed by utilizing the disclosed invention. As such, the present invention is not limited to head lice, but extends to the various species of ectoparasites that may be affected by the methods disclosed herein. Examples may include various species of lice, including head and body lice, as well as, without limitation, ticks, fleas, crab lice, mites, parasitic flies, etc.

The inventors have discovered a very effective method for killing head lice and their eggs. They have found that heated air delivered at high volumes increases the mortality rate of lice eggs and hatched lice. This discovery has the added advantages of eradicating or eliminating ectoparasite infestations with greater levels of safety, efficacy, speed, simplicity, and cost-effectiveness than is previously known in the art. In their in vivo studies, a significant number of hatched head lice survived after being exposed to air from a bonnet style hair dryer at 60° C. Similar results were obtained from tests utilizing a standard consumer hand-held blow dryer. Nearly all lice exposed to heated air at 59° C. with an airflow of at least 85 ft$^3$/min, however, died within 20 seconds when the heated air impinged directly on the lice. The significant survival rate in the first experiments may be due to the lower airflow associated with the bonnet style hair dryer and the hand-held blow dryer, as well as the inefficient manner in which these devices deliver heated air to those locations harboring lice and their eggs. This inefficient heated air delivery may allow lice to escape into cooler air pockets within clumps of hair matted down by the hair dryers. The inventors believe that the significantly higher mortality rate in the second experiment may be due to a combination of heated air, the high airflow rate, and the manner in which it was applied. Heated air applied in such a manner is a preferred method for treating head lice because it is non-chemical, it requires comparatively less time than shampoos or combing, and it is a method of treatment to which lice may not evolve resistance. These methods thus have the potential to become a permanent cure for head lice, worldwide.

An animal infested with an ectoparasite will generally require treatment to most if not all of the surface area of the infested region. The nature and the location of the infestation may vary greatly depending on the animal and the particular species of ectoparasite involved. For example, infested regions on a human having head lice will differ from infested regions on a dog having fleas. Given the wide variety of animals susceptible to numerous types of ectoparasitic infestations, methods of defining and treating a target area can vary dramatically. Thus the methods as described herein are merely exemplary, and are not intended to be limiting in any way.

Similarly, it is intended that all animals that experience ectoparasitic infestations and can derive benefit from these methods be included in the present scope. This may include, for example, reptiles, mammals, birds, etc. Additionally, in one embodiment of the present invention the animal is a mammal. In another embodiment, the animal is a human. In order to simplify the explanation of the present invention, and without intending to be limiting, the following discussion will be primarily directed to a human host having a head lice infestation.

FIGS. 1-4 and 6 schematically depict possible steps for method embodiments of the present invention. Not every step depicted is necessarily performed for a given embodiment. Similarly, the order of the steps as shown is not intended to be limiting, and it is to be understood that variations in order are considered to be within the scope of the present invention.

As shown in FIG. 1, the present invention may be embodied as a method 10 for eliminating an ectoparasite infestation. The method may comprise steps of defining a target area on an animal having an ectoparasite infestation 12, heating a volume of air to a temperature to form heated air 14, applying the heated air to the target area with an airflow, such that the heated air impinges directly on substantially all ectoparasites located within the target area 16, and maintaining the heated air at the target area for a period of time sufficient to affect an ectoparasite mortality rate of at least 50% 18. Although the 50% mortality rate may be acceptable in marginal circumstances, the present invention has also demonstrated an effective mortality rate of about 100%, which is obviously preferable. In contrast, prior art techniques have not been capable of realizing an effective 50% mortality rate in situ.

Defining a target area on an animal having an ectoparasite infestation 12 may result in multiple discrete target areas, or it may result in a target area encompassing the entire infested region. Well defined target areas may facilitate the systematic application of the heated air to all infested regions of the animal, and thus help to ensure treatment of the entire animal through treatment of multiple discrete regions. In other cases, the application of the heated air may occur over broad areas of the animal or multiple areas simultaneously.

Heating a volume of air to a temperature to form heated air 14 may be accomplished by any means known to one skilled in the art, as long as sufficient heat can be maintained in an airflow of heated air to allow the eradication of head lice. Any temperature of heated air that is effective at eliminating head lice is considered to be within the scope of the present invention. In one embodiment, the temperature of the volume of air is at least 50° C. An upper limit for temperature may be dependent on the heat endurance of the infested animal. Also, pain and discomfort thresholds are highly variable among individual humans, and thus the maximum useful temperature would be similarly variable. It is also recognized that maximum useful temperature may be different for nonhuman animals. The heat endurance of the animal may also vary with the duration of application, as higher temperatures may be tolerated for shorter periods of time than what would be typically used for lower temperatures. In one embodiment, the temperature of the volume of air can be from about 50° C. to about 100° C. In another embodiment, the temperature of the volume of air can be from about 54° C. to about 65° C. In another embodiment, the temperature of the volume of air can be from about 54° C. to about 59° C. In yet another embodiment, the temperature of the volume of air can be about 59° C.

The heated air may be applied to the target area 16 by any means known to one skilled in the arts, as long as the airflow of heated air can be maintained at a sufficient rate to allow the eradication of head lice. Any airflow that is effective at eliminating head lice is considered to be within the scope of the present invention. As with the application of heat, an upper limit to airflow may be dependent on the endurance of the infested animal. Airflow that can be tolerated by an animal will vary depending on the species. For example, pachyderms may tolerate very high airflow as compared to humans or birds. In one embodiment of the present invention, the airflow is from about 25 $ft^3$/min to about 2000 $ft^3$/min. In another embodiment, the airflow is from about 30 $ft^3$/min to about 430 $ft^3$/min. In yet another embodiment, the airflow is from about 35 $ft^3$/min to about 285 $ft^3$/min.

The heated air can also be applied to the target area by systematically applying the heated air to the target area utilizing a device to separate and lift hair. This device can be any means known to one skilled in the art that can separate and lift hair while applying heated air to ensure that substantially all regions of the target area have been thoroughly heated. In one aspect, the device can be a comb device. The comb device can be attached to the device delivering the heated air or it can be separate. The inventors have found that utilizing such a comb device can increase the effectiveness of the treatment regardless of the length of the hair. One example of the comb device is described below in more detail.

In one embodiment of the present invention, the heated air may be maintained at the target area for a period of time sufficient to affect an ectoparasite mortality rate of at least 50% 18. It is intended that the period of time include continuous and discontinuous periods. For example, heated air can be maintained continuously at the target area until at least 50% mortality rate has been achieved. In another example, heated air can be delivered to the target area in multiple applications, such that the combined effect of the multiple applications achieves a mortality rate of at least 50%. The intervening time period between applications can be seconds, minutes, hours, days, weeks, etc.

Though mortality rates of at least 50% are disclosed, the inventors have discovered that proper application of the methods disclosed herein will result in the complete elimination of ectoparasitic infestations, particularly those involving head lice. Specific embodiments do, however, contemplate lower mortality rates. In these cases, it may be acceptable to obtain these lower mortality rates while treating the infested individual multiple times, as described above. For example, in an embodiment where a treatment results in a 50% mortality rate, repeating the procedure for multiple days may produce acceptable results. As such, in one embodiment the heated air is maintained at the target area for a period of time sufficient to affect an ectoparasite mortality rate of at least 70%. In another embodiment the heated air is maintained at the target area for a period of time sufficient to affect an ectoparasite mortality rate of at least 85%. In yet another embodiment the heated air is maintained at the target area for a period of time sufficient to affect an ectoparasite mortality rate of at least 95%.

The time period that heated air may be maintained to provide an acceptable ectoparasite mortality rate can be highly variable depending on several factors, including temperature, airflow, coarseness and length of hair, the type of ectoparasite, and how directly the heated air impinges on ectoparasites within the target area. It is well within the ability of one of ordinary skill in the art to evaluate the circumstances of a particular infestation and to time the application of the heated air accordingly. In those cases where the target area comprises multiple discrete target areas, the temperature of the heated air may be maintained at each target area for at least the specified period of time. In one embodiment of the present invention, the heated air may be maintained at the target area for from about 5 seconds to about 1 hour. Obviously this time period may be further limited by the endurance of the infested individual. In another embodiment, the heated air may be maintained at the target area for from about 10 seconds to about 30 minutes. In yet another embodiment, the heated air may be maintained at the target area for from about 20 seconds to about 60 seconds.

One skilled in the art in possession of these methods would appreciate that no single factor recited above would allow the total elimination of a head lice infestation. Rather, it is a combination of the various factors recited herein that produces these surprisingly effective results. As described above, these factors include temperature, airflow, exposure duration, and direct impingement. For example, if heated air having a temperature and an airflow within an acceptable range are delivered to a target area, but the head lice are able to burrow into a bundle of hair and thus escape direct impingement of the heated air, they may survive the treatment. The inventors stress that it is the combination of these factors that greatly increase the efficacy of this treatment regimen over the prior art.

Figure 2:
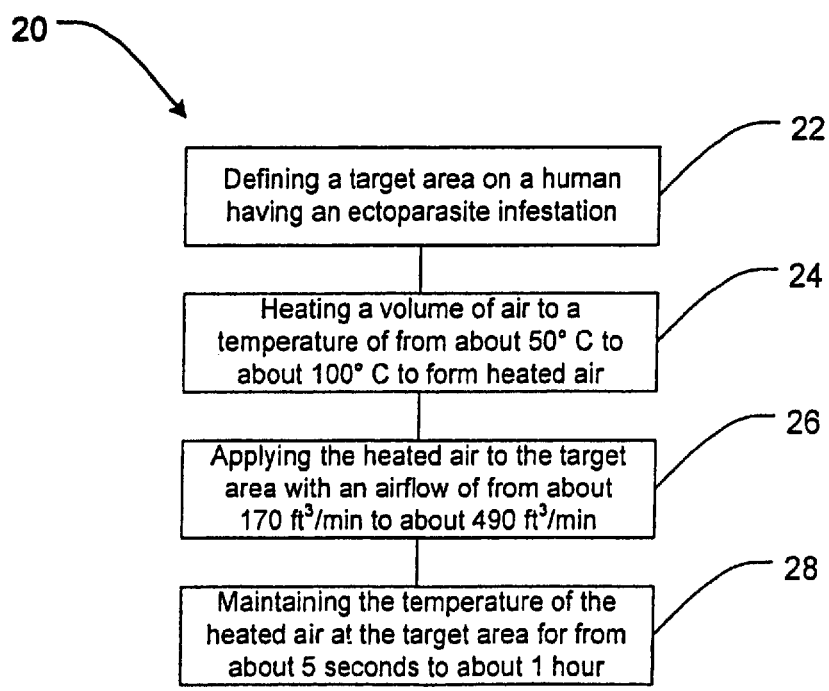
FIG. 2 is a flow chart of a method of eliminating head lice in accordance with an embodiment of the present invention.

As shown in FIG. 2, one embodiment of the present invention provides for an institutional method for eliminating an ectoparasite infestation 20. It is within the institutional environment that the present methods have demonstrated their greatest effectiveness, representing a significant advance over prior art techniques. It is intended that institutional refer to hospitals, clinics, schools, prisons, immigration offices, or any other locations known to one skilled in the art where it would be beneficial to treat lice infestations. Also, it is not intended that devices utilized in the institutional method be limited in any way. For example, an institutional device can be handheld, wall mounted, desk mounted, mounted on castors or wheels, or any other configuration known to one skilled in the art. That being said, the method can comprise steps of defining a target area on a human having an ectoparasite infestation 22, heating a volume of air to a temperature of from about 50° C. to about 100° C. to form heated air 24, applying the heated air to the target area with an airflow of from about 45 $ft^3$/min to about 365 $ft^3$/min 26, such that the heated air impinges directly on substantially all ectoparasites located within the target area, and maintaining the heated air at the target area for from about 5 seconds to about 1 hour 28.

As described above, defining a target area on a human having an ectoparasite infestation 22 may result in multiple discrete target areas, or it may result in a target area encompassing the entire infested region. Well defined target areas may facilitate the systematic application of the heated air to all infested regions of the human, and thus help to ensure treatment of the entire infested region of the human through treatment of multiple discrete regions. In other cases, the application of the heated air may occur over broad areas of the human, or multiple areas simultaneously.

One particular advantage to treating an ectoparasite infestation in an institutional setting is the performance of the treatment by an experienced clinician. The inventors have discovered that mortality rates of ectoparasites tend to increase with the experience of the individual performing the treatment. One explanation for this may be that the experienced clinician is better able to ensure that the entire infested area is thoroughly treated. If a region is missed during a treatment, ectoparasites from that region will spread, causing a rapid reinfestation.

Heating a volume of air to a temperature of from about 50° C. to about 100° C. to form heated air 24 may be accomplished by any means known to one skilled in the art, as long as sufficient heat can be maintained in an airflow of heated air to allow the eradication of head lice. Care may be taken to minimize the discomfort of the human receiving the treatment due to the temperature of the heated air. The maximum temperature that may be used is likely to be dependent on the heat endurance of the infested human. Also, pain and discomfort thresholds are highly variable among individual humans, and thus the maximum useful temperature would be similarly variable. As described above, the heat endurance of the animal may also vary with the duration of application, as higher temperatures may be tolerated for shorter periods of time than what would be typically used for lower temperatures. In one embodiment, the temperature of the volume of air can be from about 54° C. to about 65° C. In another embodiment, the temperature of the volume of air can be from about 54° C. to about 59° C. In yet another embodiment, the temperature of the volume of air can be about 59° C.

In one embodiment, heated air may be applied to the target area with an airflow of from about 45 ft$^3$/min to about 365 ft$^3$/min 26, such that the heated air impinges directly on substantially all ectoparasites located within the target area. Airflows within this range tend to be above airflows that can be generated by consumer blow dryers, and are thus more aptly suited to an institutional environment. In another embodiment, the airflow can be from about 50 ft$^3$/min to about 150 ft$^3$/min.

In a further embodiment of the institutional method, the heated air can be maintained at the target area for from about 5 seconds to about 1 hour 28. In general the heated air should be maintained at each target area for a time sufficient to ensure eradication of the ectoparasites within that region. In another embodiment, the heated air is maintained at the target area for from about 10 seconds to about 30 minutes. In yet another embodiment, the heated air is maintained at the target area for from about 20 seconds to about 60 seconds. It is intended that the terms "eradication" and "elimination" refer to the infestation and not necessarily the ectoparasites themselves. It is not required that all ectoparasites be dead or physically removed from the region, though dead and physically removed ectoparasites would be within the scope of the present invention. In other words, even if a portion of the ectoparasites in a region survive but are no longer viable following treatment according to aspects of the present invention, the infestation would still be considered eradicated or eliminated. Similarly, an infestation where one or more viable ectoparasites of the same sex survived but were unable to mate due to a lack viable ectoparasites of the opposite sex would also be considered eradicated or eliminated.

Figure 3:
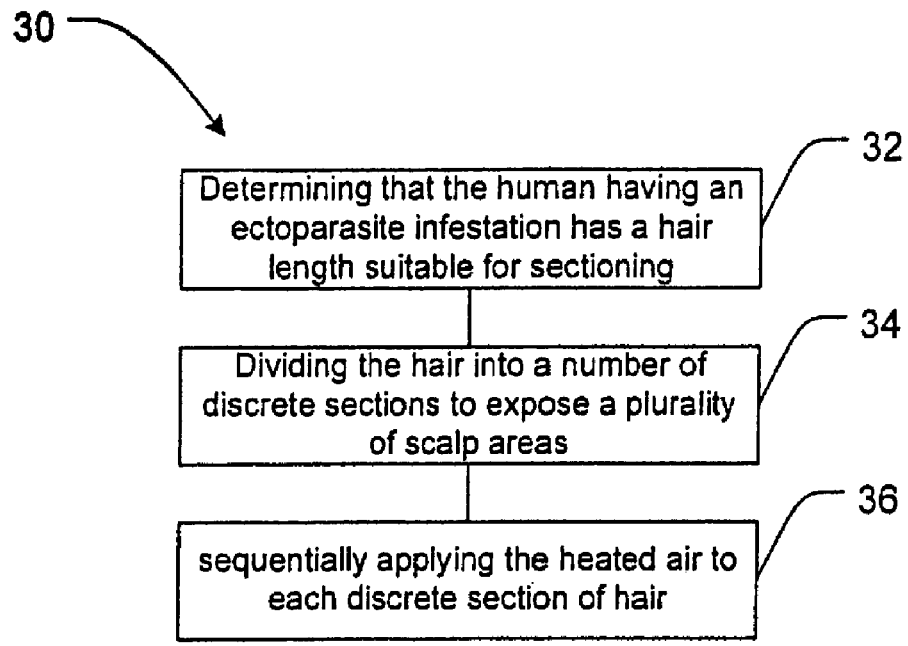
FIG. 3 is a flow chart of a method of eliminating head lice in accordance with an embodiment of the present invention.

As shown in FIG. 3, in defining a target area, the length of the individual's hair may be relevant to the eradication procedure. As such, one embodiment of the present invention may provide a method 30 including steps of determining that the human having an ectoparasite infestation has a hair length suitable for sectioning 32, dividing the hair into a number of discrete sections to expose a plurality of scalp areas 34, and sequentially applying the heated air to each discrete section of hair associated with each of the plurality of scalp areas 36. The discrete sections of hair may be separated with, without limitation, human fingers, clips, rubber bands, elastomeric fabric, wires, combs, pins, barrettes, and combinations thereof. Furthermore, the term sequentially is intended to describe a methodical, systematic order of treating the plurality of scalp sections to ensure that the entire infested area is treated, thus more efficiently eradicating the head lice infestation. The temperature of the heated air applied to each of the plurality of scalp sections may be maintained for a period of time and at an airflow as described above. Additionally, it may be beneficial to apply the heated air to multiple sides of each discrete section of hair to eradicate those head lice that may be blocked from the airflow by the sectioned hair on one side.

The inventors have found that ectoparasite mortality rates can be increased by the following method of dividing hair. This method is not intended to be limiting, but is merely provided as one example of dividing hair into discrete sections. Other methods of systematically applying heated air to all infested areas would also be considered to be within the scope of the present invention as claimed. The human's hair should be combed thoroughly with a standard comb prior to treatment to remove tangles or snarls. The hair is then parted down the middle of the scalp, and one side is clipped up with a large hair clip. On the opposite side, the hair is sectioned into squares of about 2 inches by 2 inches, for a total of about 7-10 sections on one side, depending on the thickness of the hair. One method of sectioning can begin along the part on the top of the head, beginning at the forehead, and proceed along one side of the part to the back of the neck. Each square of hair can be twisted tight at the base of the hair and secured with a standard butterfly clip. Below the first row of square sections, the remaining hair can be sectioned into similar squares around the ear. The procedure is then repeated for the other side after removing the large hair clip. Following sectioning, the treatment can be started with the lowest section in front of the ear on one side. This section is unclipped and the hair held with one hand about three inches from the scalp. It may be helpful to hold the hair loosely to facilitate the passage of the heated air. The heated air may be delivered near the surface of the scalp at an angle of about 45 degrees to the scalp. The heated air may be delivered from one direction for about 30 seconds, while holding the device delivering the heated air motionless. The hair may be held such that it parachutes out to let the heated air flow through it. The heated air is then delivered in a similar manner to the other side of the square for approximately 30 seconds. The hair is re-clipped following treatment. Each square section is treated sequentially moving back toward the neck in a similar manner, until the entire head has been treated.

Figure 4:
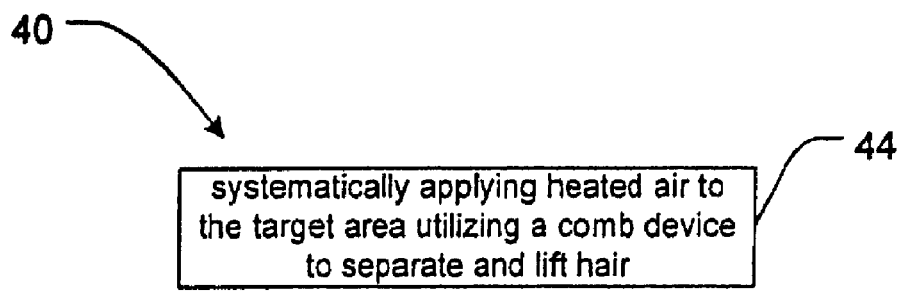
FIG. 4 is a flow chart of a method of eliminating head lice in accordance with an embodiment of the present invention.

As shown in FIG. 4, the institutional method can further include a step of 40 systematically applying heated air to the target area utilizing a device to separate and lift hair within the target area 44. The device to separate and lift hair can be a comb device. This combing method may be utilized due to the difficulties of physically sectioning shorter hair into discrete scalp sections, coarser hair, etc. It should be noted, however, that the length and coarseness of the human's hair is not limiting as to which method embodiment is utilized, and that alternative embodiments are presented solely to provide more convenient means of accomplishing the eradication of head lice. For example, short hair that may be difficult to section can still be divided into scalp sections as described in the previous embodiment without departing from the scope of the present invention. Similarly, it is contemplated that utilizing a comb device is not limited to hair that is difficult to section, and is thus contemplated in cases involving longer hair.

The inventors have discovered that ectoparasite mortality rates can be increased by the following method of utilizing a comb device. This method is not intended to be limiting, but is merely provided as one example of utilizing a comb device. Also, the following method appears to increase mortality rates for both long and short hair, and is thus not limited by hair length. The human's hair should be combed thoroughly with a standard hair comb prior to treatment in order to remove any tangles or snarls. The hair should then be parted down the middle of the scalp. The comb device can be used to introduce the heated air starting at the forehead end of the part. The teeth of the comb device should be oriented such that the heated air blows over the top of the human's head. The comb device can be slowly pulled down the side of the human's scalp, towards the sideburn. Each pass should take about two minutes such that substantially all areas of the scalp are exposed for at least 30 seconds. This speed is approximately about 1 inch in 20 seconds for many situations. These downward movements are repeated moving from the front to the back of the human's head, overlapping slightly with each pass. Next, the comb device is placed on the sideburn with the teeth facing over the ear and towards the back of the head. The comb device can be drug over and around the back of the ear at the same speed as previously described. The teeth of the comb device should be in contact with the scalp for most of the treatment. Next, with the human's head tilted forward to expose the back of the neck, the comb device is drug from the base of the neck up to the crown on the head at the speed previously described. These procedures are repeated until substantially all of the head has been covered.

Figure 5:
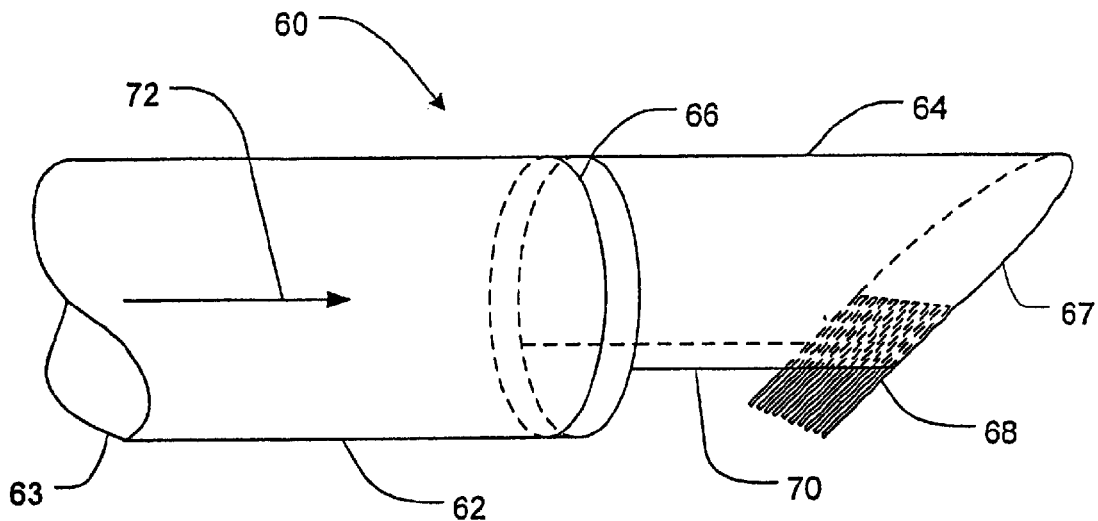
FIG. 5 is a perspective view of a comb device for lifting and separating hair.

One example of a comb device to lift and separate hair at the scalp while maintaining an airflow of heated air is shown in FIG. 5. The comb device 60 is not intended to be limiting, and is shown solely as an example of how such a device might be embodied. Any device which provides an airflow of heated air to the scalp while lifting and separating the hair would be considered to be within the scope of the present invention. Various motions are contemplated whereby a comb device can be utilized, including, without limitation, pushing motions, pulling motions, sliding motions, etc. In this embodiment, a cylindrical tube 62 may be coupled to a source of heated air at a proximal end 63, such that the heated air would flow in a direction indicated by the arrow 72. The cylindrical tube 62 may be coupled to a distal tube 64 having a beveled end 67 and an airflow opening 70. The distal tube 64 may be coupled to the cylindrical tube 62 by a connector 66 or any other attachment means known to one skilled in the art. Also, the distal tube 64 and the cylindrical tube 62 may be constructed from a single tube with an airflow opening 70 and a beveled edge 67. The comb device 60 also includes a comb 68 coupled to the beveled end 67 of the distal tube 64. The teeth of the comb 68 can be inclined in a direction that is generally opposite the general direction of airflow 72 from the tube 62. It is also contemplated that the comb can be formed from a portion of the tube. This configuration allows the heated air to flow in direction 72 from the heated air source, through the cylindrical tube 62 to the distal tube 64, and out the airflow opening 70. As such, heated air is forced out of the comb device 60 at the scalp areas as the comb 68 is lifting and separating the hair. This action in effect directs the heated air to the roots of the hair and along the length of the hair to the locations where lice often reside.

It is contemplated that any configuration of comb device known to one skilled in the art that can act to separate and lift hair would be within the scope of the present invention. These devices can include teeth oriented generally opposite to the general direction of the airflow, oriented generally in the same direction of the airflow, or any other configuration known to one skilled in the art. Opposite is intended to include orientations that are greater than 90° to the direction of the airflow.

Also, all configurations of devices to apply heated air to the target area known to one skilled in the art are considered to be within the scope of the present invention. In one aspect, heated air can be generated and blown through the hair into the room air. In another aspect, heated air can be recirculated through the device, thereby reducing the overall power demand of the device by conserving and/or reusing preheated air. Suction devices are also contemplated. It may be beneficial to apply suction opposite to the heated air in order to affect heated air recirculation and/or to more expeditiously remove dead, dying, and living lice and eggs that are shaken loose from the hair. In another aspect, a filter can be utilized in the device to catch the lice, eggs, and debris, and thus act to minimize many of the safety threats accompanying the collection and disposal of blood containing organisms.

Though it is preferred that the treatment be performed in an institutional setting in order to obtain the best possible results from the treatment, i.e. total elimination of the ectoparasite infestation, handheld methods that will most likely be used at home are also considered to be within the scope of the present invention. It is likely that handheld methods of treatment will involve devices that produce lower airflows than the institutional devices utilized in the methods described above. As such, the effectiveness of the handheld methods may be somewhat lower than what is seen in a institutional environment. In such cases, effective eradication of an ectoparasite infestation may be accomplished through multiple treatments.

Figure 6:
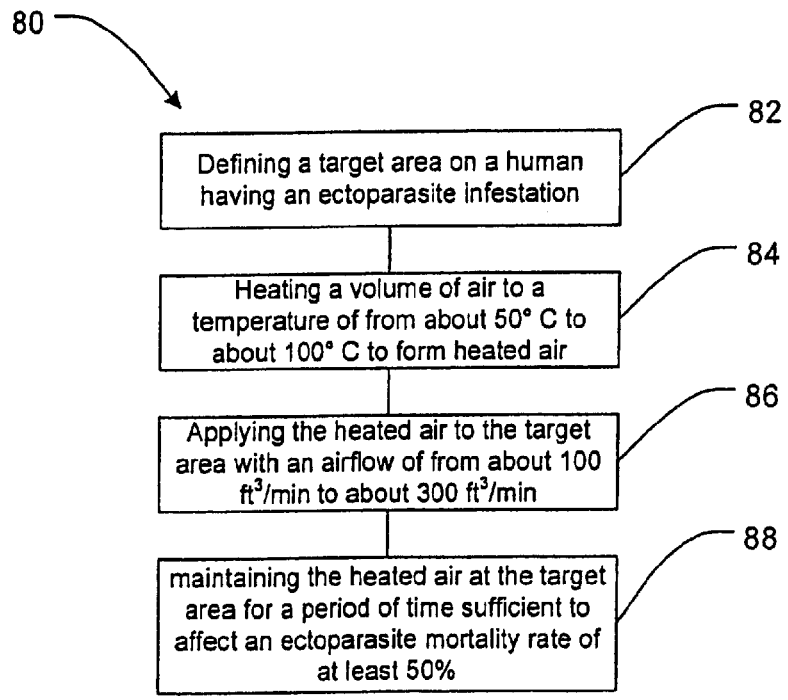
FIG. 6 is a flow chart of a method of eliminating head lice in accordance with an embodiment of the present invention.

As such, FIG. 6 shows one embodiment of the present invention that provides a handheld method for eliminating an ectoparasite infestation 80. It is intended that the term handheld refer to blow dryers and the like that can be purchased and used at home. In some cases, particular handheld blow dryers may be classified as institutional devices due to higher airflows of these particular models. This handheld method may include steps of defining a target area on a human having an ectoparasite infestation 82, heating a volume of air to a temperature of from about 50° C. to about 100° C. to form heated air 84, applying the heated air to the target area with an airflow of from about 20 ft$^3$/min to about 220 ft$^3$/min 86, such that the heated air impinges directly on substantially all ectoparasites located within the target area, and maintaining the heated air at the target area for a period of time sufficient to affect an ectoparasite mortality rate of at least 50% 88. The time period may be continuous or discontinuous, as described above.

In one embodiment of the present invention, the treatment can be performed with a blow dryer having an attached comb device. The comb device can be of any configuration known to one skilled in the art, such as, without limitation, the device 60 as shown in FIG. 5. In this case, temperature and airflow will be dependent on the particular blow dryer utilized. It is assumed, however, that temperature and airflow will be within the above recited ranges. In one embodiment of the present invention, the temperature of the volume of air can be from about 54° C. to about 65° C. In another embodiment, the temperature of the volume of air can be from about 54° C. to about 59° C. In yet another embodiment, the temperature of the volume of air can be about 59° C. Regarding airflow, in one embodiment, the airflow can be from about 25 ft³/min to about 125 ft³/min. Also, though ectoparasite mortality rates may be highly variable in handheld methods given the lower airflow and inexperience of the individual performing the treatment, in one embodiment the heated air can be maintained at the target area for a period of time sufficient to affect an ectoparasite mortality rate of at least 70%. In another embodiment the heated air is maintained at the target area for a period of time sufficient to affect an ectoparasite mortality rate of at least 85%. In yet another embodiment the heated air is maintained at the target area for a period of time sufficient to affect an ectoparasite mortality rate of at least 95%. These mortality rates may be the result of a single treatment or they may be the combined rates following multiple treatments.

Given the lower airflow rates of some blow dryers, the comb device may allow the hair to be lifted and separated and thus further facilitate the delivery of the heated air directly to the ectoparasites within the infested region. Note that the comb device 60 of FIG. 5 is oriented such that the hair is lifted and separated by a pulling motion rather than the pushing motion of current standard blow dryer attachments. Other embodiments may include comb devices utilizing push motions, which are also considered to be within the scope of the present invention.

As has been discussed above, previous inaccurate airflow ranges were obtained through the use of a pitot tube anemometer. Such devices utilize a velocimetric method for measuring airflow. Velocimetric flow is given as the linear movement of gas per unit time, with feet per second (fps) being a common unit. The use of velocimetric data may be employed in some cases because the measurement of air velocity can be readily undertaken by the use of simple devices. Once the velocity of airflow is determined, the linear data is converted into volumetric data by integrating over the cross-sectional area of the conduit, i.e. multiplying the cross-sectional area of the conduit by the linear airflow. It appears that this measurement technique may result in a high degree of inaccuracy because the linear airflow is both nonlaminar (i.e. is not always directed straight downstream) and inconsistent (i.e. is not a constant velocity across the section of the conduit). Thus, velocimetric airflow may not be a reliable method of describing airflow in most applications.

Alternatively, volumetric airflow is given as volume passing a specific point or plane per unit time, with a common unit being cubic feet per minute (ft³/min or cfm). The inventors believe that volumetric airflow measurements may be a more accurate means of describing airflow since cross-sectional nonlaminarity and velocity inconsistency do not grossly affect the resulting data. This is because volumetric airflow is the amount of air volume passing through a conduit per unit time, regardless of microcurrent movement. It is believed that such volumetric measurements may provide a more accurate description of reported airflow range values. Non-limiting methods for measuring volumetric airflow are described in the Examples below.

EXAMPLES

The following examples of airflow measurement methods are provided to promote a more clear understanding of certain embodiments of the present invention, and are in no way meant as a limitation Example 1

A pitot tube anemometer (Dwyer model 166-12 pitot tube connected to a TSI DP-Calc™ digital micromanometer) was utilized to measure the airflow of a standard hair blow dryer. A linear airflow velocity (in ft/min) was measured at 24 points across the orifice of the blower and a "correction factor" was determined that related the airspeed in the center of the orifice to the average airspeed across the orifice. One hundred airspeed measurements were then taken in the center of the orifice, and averaged. The correction factor was then applied to the average airspeed. The corrected airspeed was then multiplied by the cross-sectional area of the orifice to give volumetric airflow in cfm.

The measured airflow for the hair blow dryer was 170 cfm using the pitot tube. Because the airflow was partially obstructed by heating elements near the outlet orifice, the airflow was normalized by attaching a 2-foot length of 1½ inch inside diameter PVC pipe to the outlet orifice. In this way, it was envisioned that the airflow would enter the pipe in a turbulent flow but would achieve normalized, semi-laminar flow by the end of the pipe. The velocimetric airflow was then determined as described above and converted to volumetric airflow. This measurement is shown in Table 1.

Example 2

The pitot tube anemometer and linear airflow velocity measurement method of Example 1 was utilized to measure the airflow of a wall-mounted blower of the type used to dry hands in a restroom. The measured airflow for the Wall Mounted blower was 490 cfm. This airflow was taken directly at the orifice of the blower. This measurement is shown in Table 1.

Example 3

The pitot tube anemometer and linear airflow velocity measurement method of Example 1 was utilized to measure the airflow of a custom built blower, herein labeled custom blower 1. The measured airflow for this device was 450 cfm. This airflow was determined by placing the pitot tube directly in the airstream after a full length of flexible hosing (65 inches). A temperature of 55° C. was measured at the hose orifice. The ambient room air temperature was ~25° C. and ambient room relative humidity was ~50%. This measurement is shown in Table 1.

Example 4

The pitot tube anemometer and linear airflow velocity measurement method of Example 1 was utilized to measure the airflow of a custom built blower, herein labeled custom blower 2. The measured airflow for this device was 361 cfm. This airflow was determined by placing the pitot tube directly in the airstream after a full length of hosing (65 inches) with the internal temperature set at 63° C. through the use of a closed-loop digital temperature controller. This results in a 59° C. temperature at the hose outlet orifice (temperature decline due to conductive and radiative heat loss through the hose wall). The ambient room air temperature was ~25° C. and ambient room relative humidity was ~50%. This measurement is shown in Table 1.

Example 5

Airflow measurements were determined by a Bulk Volumetric method as follows: A large bag was constructed out of plastic. Specifically, 40 inch continuous polyethylene tube stock (40 inches wide, or ~25.5 inches in diameter), 0.004 inch thick, was cut to a length of 181.5 inches. The ends were sealed with adhesive packaging tape, except for a small opening in the corner of one end of the bag corresponding to a diameter of approximately 2.5 inches. The fully inflated bag was modeled using a 3D parametric CAD system by first inflating the bag and taking measurements of the outside bag dimensions. Using this model, the inflated volume of the bag was calculated at 83,000 cubic inches +/−~5%. Each of the devices of Examples 1-4 were separately used to inflate the fully collapsed bag through the small end opening and the time to complete inflation was recorded. These measurements were iterated 10 times with each device and the average time of inflation was calculated. The volume of the bag was then divided by the average time required to fill the bag to give airflow in cfm. These measurements are shown in Table 1.

Example 6

Airflow measurements were determined by a Bernoulli's orifice flow meter method as follows: A Bernoulli's flow meter was constructed from PVC pipe and a precision thin steel plate. Each of the blower devices of Examples 1-4 were attached to the flow meter and a pressure difference was taken in chambers on either side of the plate. A Bernoulli's equation written in Microsoft Excel converted the air pressure difference to velocimetric airflow. The equation was then used to convert each pressure difference to airflow in cfm. These measurements are shown in Table 1.

TABLE 1

Measured airflow values for Examples 1-7

| Device | Manufacturer Reported Value | Pitot Tube | Bulk Volumetric | Bernoulli's Flow Meter |
|---|---|---|---|---|
| Bonnet-style Dryer | — | — | 9 | 10 |
| Blow Dryer A | 580 | 170 | 41 | 33 [Note 1] |
| Blow Dryer B | 170 | — | 102 | — |
| Wall Mounted | 170 | 490 | 103 | [Note 2] |
| Custom blower 1 | 720 [Note 4] | 450 | 113 | [Note 3] |
| Custom blower 2 | 720 [Note 4] | 361 | 88 | 93 |
| Low-power custom blower | 360 [Note 4] | — | 87 | 89 |

[Note 1] the blow dryer lost a small amount of airflow through the rear of the fan housing.
[Note 2] the housing of the wall mounted blower was designed to vent air elsewhere when pressure increased at the outlet orifice, so this method was inapplicable.
[Note 3] the custom blower 1 had too high an airflow to be measured with the flow meter used.
[Note 4] these values were calculated from velocimetric data provided by the manufacturer.

As has been stated, the airflows originally reported in the previously filed U.S. patent application Ser. No. 11/133,067 were measured using a pitot tube anemometer. Table 1 shows data measuring the same airflows using at least two different methods described above. Airflow data from a bonnet-style hair dryer and from a low-power custom blower have also been included. The Bulk Volumetric method is simple and greatly reduces both experimental and calculational error. The Bernoulli's Thin Plate Orifice Flow-meter method was used to validate the data derived from the Bulk Volumetric method for those devices for which the flow meter method could be utilized. Because these two methods utilize different principles yet the values obtained generally correlate to within +/−5 cfm (~5%) of each other, these values may be more accurate and consistent than the values reported in the previous application.

Example 7

Manufacturer A reported an airflow of 580 cfm for blow dryer A. Manufacturer B reported an airflow for a substantially more powerful blow dryer B to be 170 cfm. The Bulk Volumetric method of Example 5 was utilized to measure the respective airflows from blow dryers A and B. The airflow of blow dryer A was measured to be ~41 cfm, while the airflow of blow dryer B was measured to be ~102 cfm. Thus the Bulk Volumetric method measured relative airflows from the blow dryers as expected, with the substantially more powerful blow dryer having the higher airflow.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the present invention.

The invention claimed is:

1. A method for eliminating an ectoparasite infestation, comprising steps of:
    defining a target area on an animal having an ectoparasite infestation, said target area including the animal's hair and the animal's scalp; heating a volume of air to a temperature to form heated air at a temperature of from about 54° C. to about 65° C.;
    applying the heated air to the target area with an airflow such that the heated air impinges directly on substantially all ectoparasites located within the target area, and wherein the heated air is applied directly to the animal's hair and animal's scalp such that at least a substantial portion of the heated air is forced directly at and directly contacts the animal's scalp from a device for delivering the heated air; and
    maintaining the heated air at the target area for a period of time and at a sufficient airflow to affect an ectoparasite mortality rate of at least b 50%.

2. The method of claim 1, wherein the animal is a human.

3. The method of claim 1, wherein the temperature of the volume of air is from about 54° C. to about 59° C.

4. The method of claim 1, wherein the heated air is maintained at the target area for from about 5 seconds to about 1 hour.

5. The method of claim 4, wherein the heated air is maintained at the target area for from about 10 seconds to about 30 minutes.

6. The method of claim 5, wherein the heated air is maintained at the target area for from about 20 seconds to about 60 seconds.

7. The method of claim 1, wherein the heated air is maintained at the target area for a period of time sufficient to affect an ectoparasite mortality rate of at least 70%.

8. The method of claim 7, wherein the heated air is maintained at the target area for a period of time sufficient to affect an ectoparasite mortality rate of at least 95%.

9. The method of claim 1, wherein the step of applying the heated air to the target area further includes systematically applying the heated air to the target area utilizing a device to separate and lift hair within the target area.

10. The method of claim 9, wherein a comb device is used to separate and lift the hair.

11. An institutional method for eliminating an ectoparasite infestation, comprising:
    defining a target area on a human having an ectoparasite infestation, said target area including the human's hair and the human's scalp;

heating a volume of air to a temperature of from about 54° C. to about 65° C. to form heated air; and applying the heated air to the target area such that the heated air impinges directly on substantially all ectoparasites located within the target area, and wherein the heated air is applied directly to the human's hair and the human's scalp such that at least a substantial portion of the heated air is forced directly at and directly contacts the human's scalp from a device for delivering the heated air.

12. The method of claim 11, wherein the temperature of the volume of air is from about 54° C. to about 59° C.

13. The method of claim 11, wherein the heated air is delivered at an airflow of from about 25 cfm to about 125 cfm.

14. The method of claim 11, wherein the heated air is maintained at the target area for from about 10 seconds to about 30 minutes.

15. The method of claim 11, further comprising steps of: determining that the human having an ectoparasite infestation has a hair length suitable for sectioning;
dividing the hair into a number of discrete sections to expose a plurality of scalp areas; and
sequentially applying the heated air to each discrete section of hair associated with each of the plurality of scalp areas.

16. A handheld method for eliminating an ectoparasite infestation, comprising:

defining a target area on a human having an ectoparasite infestation, said target area including the human's hair and the human's scalp;

heating a volume of air to a temperature of from about 54° C. to about 65° C. to form heated air; and applying the heated air to the target area from a handheld device for delivering the heated air such that the heated air impinges directly on substantially all ectoparasites located within the target area, and wherein the heated air is applied directly to the human's hair and the human's scalp such that at least a substantial portion of the heated air is forced directly at and directly contacts the human's scalp from the handheld device.

17. The method of claim 16, further comprising maintaining the heated air at the target area for a period of time sufficient to affect an ectoparasite mortality rate of at least 95%.

18. The method of claim 16, wherein the temperature of the volume of air is from about 54° C. to about 59° C.

19. The method of claim 16, wherein the step of applying the heated air to the target area further includes systematically applying the heated air to the target area utilizing a comb device to separate and lift hair within the target area.

20. The method of claim 16, wherein the heated air is applied to the target area with an airflow of from about 20 cfm to about 125 cfm.

* * * * *